United States Patent
Day et al.

(10) Patent No.: US 6,926,916 B1
(45) Date of Patent: Aug. 9, 2005

(54) CHEWING GUM COMPOSITIONS

(75) Inventors: Trevor Neil Day, Windsor (GB); Donald James White, Jr., Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 490 days.

(21) Appl. No.: 09/831,462

(22) PCT Filed: Jun. 22, 2000

(86) PCT No.: PCT/US00/17177

§ 371 (c)(1), (2), (4) Date: May 9, 2001

(87) PCT Pub. No.: WO01/39606

PCT Pub. Date: Jun. 7, 2001

Related U.S. Application Data

(60) Provisional application No. 60/165,351, filed on Nov. 12, 1999, and provisional application No. 60/180,352, filed on Feb. 4, 2000.

(51) Int. Cl.$^7$ .............................. A23G 3/30; A61K 9/68
(52) U.S. Cl. .............................. 426/3; 424/48; 424/440
(58) Field of Search .......................... 426/3, 5; 424/48, 424/440

(56) References Cited

U.S. PATENT DOCUMENTS

| | | | | |
|---|---|---|---|---|
| 4,808,401 A | * | 2/1989 | Gaffar et al. | 424/52 |
| 4,889,712 A | * | 12/1989 | Gaffar et al. | 424/52 |
| 5,702,687 A | * | 12/1997 | Miskewitz | 424/440 X |
| 5,833,954 A | * | 11/1998 | Chow et al. | 424/440 X |

FOREIGN PATENT DOCUMENTS

| | | | |
|---|---|---|---|
| WO | 95/07683 | * | 3/1995 |

* cited by examiner

*Primary Examiner*—Arthur L. Corbin
(74) *Attorney, Agent, or Firm*—Emelyn DeLeon Hiland

(57) ABSTRACT

The present invention relates to chewing gum composition comprising a polymeric surface active agent. A second aspect of this invention relates to a crunchy chewing gum wherein the crunchy texture is provided by particulate polyphosphate particles within the formulation and which lasts through the initial minutes of mastication. The chewing gum composition may also contain a cationic material and or an orally active metallic ion. The chewing gum composition will provide surface conditioning effects on a subject's teeth and or oral mucosa and the crunchy texture is used as a sensate to reinforce these effects. The surface conditioning effects can be measured through in vitro or in vivo testing. The in vitro testing shows a total surface energy and or a lewis base score to increase immediately after treatment with the chewing gum and then decrease over time. The in vivo testing shows a water contact angle of the oral mucosa to decrease after treatment with the chewing gum composition and/or a significantly higher smooth teeth feel relative to other chewing gum compositions. The present invention also relates to methods of providing surface conditioning effects to a subject comprising administering to the subject a chewing gum comprising a polymeric surface active agent. The present invention also relates to methods of reducing astringency of a chewing gum containing an orally active metallic ion without significantly reducing the efficacy of the metallic ion.

37 Claims, No Drawings

CHEWING GUM COMPOSITIONS

This application claims the benefit of U.S. Provisional Application No. 60/165,351 filed Nov. 12, 1999 and U.S. Provisional Application No. 60/180,352 filed Feb. 4, 2000.

BACKGROUND OF THE INVENTION

The present invention relates to chewing gum compositions containing polymeric surface active agents, including polyphosphates. These polymeric surface active agents may provide novel surface conditioning reaction to oral surfaces such as the teeth and mucosa. This leads to improved cleaning impression. The present invention further relates to compositions wherein the chewing gum has a crunchy texture conferred to it by the polyphosphate particles.

Polymeric surface active agents, such as polyphosphates, are known in the oral care art. Although disclosed in chewing gum compositions, these ingredients are most commonly found in dentifrice compositions. Polyphosphates are known to provide an anti-calculus benefit as stated in U.S. Pat. Nos. 5,094,844, 4,808,401 and EP 0333301 issued to Gaffar et al.. Polyphosphates are also know to provide a buffering effect within zinc comprising oral compositions as stated in U.S. Pat. Nos. 4,170,632 and 4,170,633 both to Wagenknecht, deceased et al. Other chewing gum patents disclosing a polyphosphate include U.S. Pat. No. 5,702,687 issued to Miskewitz and EP0,387,024 issued to McClanahan.

Prior art also exists wherein particulate matter has been incorporated into chewing gum compositions such that the resultant product does have a somewhat "crunchy" texture. For example chewing gums with a "crunchy" exterior coating have been previously disclosed such as the hard sugar coated gums disclosed in U.S. Pat. Nos. 4,486,511 and 4,792,453 and gums with surface printed solid particles disclosed in U.S. Pat. No. 3,962,463. Such disclosures are limited to a "crunchy" exterior surface of the gum and thus do not provide an overall texture sensation. Furthermore, confectionery gums wherein sugars and sugar substitutes (such as isomalt, candy and the like), sometimes in conjunction with freeze dried food stuffs, are distributed throughout the body of the gum for the purpose, at least in part, of providing a "crunchy" texture are also known (FR 2,748,902; GB 950,811; EP 017,691; U.S. Pat. Nos. 5,958,472, and 5,017,385). Whilst these latter disclosures do provide useful advances in conferring a "crunchy" sensation to the gum they do so by the use of food stuffs and not by use of the oral care active itself.

Surprisingly, research has now revealed additional benefits of chewing gums containing polymeric surface active agents, particularly when the polymeric surface active agent is a polyphosphate, even more particularly a particulate polyphosphate. These new benefits are related to effects on the surface chemical characteristics of mucosal and tooth surfaces which provide remarkable cleaning impression and positive mouth feel characteristics for extended periods of time during and following use. These effects have now been shown to be correlated to effects on oral surface energy characteristics including modification of surface hydrophilic and hydrophobic properties. Additionally, when certain polyphosphates, particularly of a particulate nature, are incorporated within the gum they can confer a "crunchy" texture to the product which lasts throughout the initial minutes of mastication and which reinforces for the consumer the oral care benefit of the product. Furthermore, due to the soluble nature of the polyphosphate materials the "crunchy" texture disappears over time leaving no gritty residue.

The surface conditioning effects can measured using several different methods. The surface conditioning effects on a subject's teeth and oral mucosa can be measured in vivo. These measurements include consumer responses on questions concerning clean teeth and smooth teeth. Other in vivo measurement include the water contact angle on the tooth surface and on the mucosa surfaces. The surface conditioning effects can also be measured in considerable detail through in vitro methods. In vitro methods are made over time to measure surface free energies and pellicle film thickness and composition.

It has also been found that the polymeric surface active agent can help to reduce the astringency of a metallic ion. Additionally, this reduction in astringency can occur without significantly reducing the efficacy of the metallic ion and without significantly reducing the efficacy and the surface conditioning effects of the polymeric surface active agent.

It is an object of the present invention to provide chewing gum compositions containing polymeric surface active agents which provide improved intraoral cleaning impression and smooth tooth surface impression derived from the chemical control of tooth and mucosal surface energy characteristics.

It is an object of the present invention to provide chewing gum compositions comprising polymeric surface active agents, cationic material, and/or orally active metallic ions.

It is also an object of the present invention to provide chewing gum compositions with reduced astringency, but wherein the efficacy of the chewing gum is not significantly reduced.

It is a further object of this invention to provide a chewing gum which has a "crunchy" texture during the initial minutes of mastication disappearing over time to leave no gritty residue and wherein this "crunchy" texture is provided by a polyphosphate.

These and other objects of the present invention will become readily apparent from the detailed description which follows.

All percentages and ratios used herein are by weight of the specific chewing gum composition, unless otherwise specified. All measurements are made at 25° C., unless otherwise specified.

SUMMARY OF THE INVENTION

A first aspect of this invention relates to a chewing gum composition comprising a polymeric surface active agent. The chewing gum composition may also contain a cationic material and/or an orally active metallic ion. The chewing gum composition will provide surface conditioning effects on a subject's teeth and/or oral mucosa. The surface conditioning effects can by measured through in vitro or in vivo testing. The in vitro testing shows a total surface energy and/or a lewis base score to increase immediately after treatment with the chewing gum and then decrease over time. The in vivo testing shows a water contact angle of the oral mucosa to decrease after treatment with the chewing gum composition and/or a significantly higher smooth teeth feel relative to other chewing gum compositions. The present invention also relates to methods of providing surface conditioning effects to a subject comprising administering to the subject a chewing gum comprising a polymeric surface active agent. The present invention also relates to methods of reducing astringency of a chewing gum containing a metallic ion without significantly reducing the efficacy of the metallic ion.

According to a second aspect this invention relates to a chewing gum composition which has a crunchy texture wherein the crunchy texture is conferred to the gum by the inclusion of particulate polyphosphate material within the composition. The "crunchy" texture can be attained when the polyphosphate material used has a particle size of between 100 μm and 2000 μm. Furthermore, by ensuring that the polyphosphate is at least sparingly soluble the "crunch" will slowly disappear to leave a non gritty gum.

DETAILED DESCRIPTION OF THE INVENTION

The chewing gum compositions of the present invention may be in the form of a conventional chewing gum or any other product form which is suitable for chewing. Suitable physical forms include sticks, dragees, chiclets, and batons. The chewing gum may also be a digestible or dissolvable gum suitable for chewing. A chewing gum is typically retained in the oral cavity for a time sufficient to allow ingredients released to contact substantially all of the dental surfaces and/or oral tissues for purposes of oral activity.

The term "carrier materials" as used herein means any safe and effective additional chewing gum components used in the chewing gum compositions of the present invention. Such materials include abrasive polishing materials, elastomers, resins, plasticisers, fats, solvents, waxes, emulsifiers, softeners, bulking agents, sweeteners, absorbents, orally active metallic ions, cationic material, fluoride ion sources, additional anticalculus agents, antimicrobial agents, buffers, whitening agents, alkali metal bicarbonate salts, thickening materials, humectants, water, surfactants, titanium dioxide, flavoring agents, xylitol, coloring agents, and mixtures thereof.

The present compositions comprise essential components, as well as optional components. The essential and optional components of the compositions of the present invention are described in the following paragraphs.

Polymeric Surface Active Agent

The present invention includes a polymeric surface active agent. The agents will provide the surface conditioning effects. These agents may also be tartar control or anticalculus agents and may also provide stain control and reduction in plaque. The polymeric surface active agents will also provide a clean teeth and longer lasting clean teeth and mouthfeel.

The polymeric surface active agents include any agent which will produce the desired surface conditioning effects. The desired surface conditioning effects include the desorption of adsorbed pellicle proteins and creating a hydrophilic tooth surface immediately after treatment. These surface conditioning effects are measured through in vitro methods over time. The agents will also create several related surface conditioning effects which are measured through in vivo testing done over time. The effects include creating an increased hydrophilic surface on the tooth surface and a hydrophobic surface on the oral mucosa as measured by changed water contact angles. It is thought that these measurements will correlate with consumers noticing a cleaning impression.

The polymeric surface active agents include the phosphorylated polymers, polyelectrolyes, and acrylate polymers. Additional polyelectrolyes include the antibacterial enhancing agents described in U.S. Pat. Nos. 5,032,386 and 5,840,281, both to Gaffar et al. A preferred polymeric agent is polyvinylphosphonic acid. Other suitable polymeric surface active agents include the polymers described in U.S. Pat. Nos. 5,292,501; 5,213,789; 5,093,170; 5,009,882; and 4,939,284; all to Degenhardt et al. and U.S. Pat. No. 5,011,913 to Benedict et al. A preferred polymer is diphosphonate modified polyacrylic acid. Polymers with activity must have sufficient surface binding propensity to desorb pellicle proteins and remain affixed to intraoral surfaces. For tooth surfaces, polymers with end or side chain phosphate or phosphonate functions are preferred, although other polymers with mineral binding activity may prove effective depending upon adsorption affinity.

The preferred polymeric surface active agent is a polyphosphate. A polyphosphate is generally understood to consist of two or more phosphate molecules arranged primarily in a linear configuration, although some cyclic derivatives may be present. Although pyrophosphates and tripolyphosphate are a polyphosphates, the polyphosphates desired are those having around four or more phosphate molecules so that one or more internal phosphate groups may be present. The pyrophosphates are discussed separately under anticalculus agents. The inorganic polyphosphate salts desired include tetrapolyphosphate and hexametaphosphate, among others. Polyphosphates larger than tetrapolyphosphate usually occur as amorphous glassy materials. Preferred in this invention are the linear "glassy" polyphosphates having the formula:

$$XO(XPO_3)_nX$$

wherein X is sodium, potassium, or hydrogen and n averages from about 6 to about 125. For use in the second aspect of this invention it is preferred that the particulate polyphosphate is sodium polyphosphate with an average chain length of from about 10 to about 30, preferably from about 15 to 25, more preferably from about 21 to about 23. Preferred are polyphosphates manufactured by FMC Corporation which are commercially known as Sodaphos (n≈6), Hexaphos (n≈13), and Glass H (n≈21). Hexaphos and Glass H are preferred with Glass H being the most preferred polyphosphate. These polyphosphates may be used alone or in an combination thereof. The phosphate sources are also described in more detail in Kirk & Othmer, *Encyclopedia of Chemical Technology*, Fourth Edition, Volume 18, Wiley-Interscience Publishers (1996), incorporated herein by reference in its entirety, including all references incorporated into Kirk & Othmer.

The amount of polymeric surface agent required is an effective amount to provide the surface conditioning effects and, if desired, according to a second aspect of the invention, to provide a "crunchy" texture. An effective amount of a polymeric surface active agent will typically be from about 0.1% to about 50%, preferably from about 1% to about 35%, more preferably from about 2% to about 25%, and most preferably from about 5% to about 15% by weight of the total chewing gum composition. In addition to creating the surface conditioning effects, the polymeric surface active agent has been found to associate with orally active metallic ions or species whilst maintaining their solubility and efficacy. For example, the polymeric surface active agent may form a complex with stannous fluoride or zinc and still provide the desired tartar control, stain control, and surface conditioning, in addition to not significantly prohibiting the efficacy of the stannous fluoride or zinc. The polymeric surface active agents may enhance the solubility of orally active metallic ions, such as zinc salts and stannous salts. The orally active metallic ions may provide several efficacious benefits to the chewing gum such as reduced gingivitis, plaque, and sensitivity and improved breath. In addition to not significantly reducing the efficacy of an orally active metallic ion, the polymeric surface active agents, particularly sodium polyphosphate, may reduce the amount of astringency created by the orally active metallic ion. This may be due to lower levels of mucosal protein precipitation in the mouth. This can be measured by in vivo testing and sensory scores. The preferred orally active metallic ions are zinc and tin or stannous. The orally active metallic ions are typically present in an amount of from about 0.01% to about 10%, preferably from about 0.05% to about 5%, more preferably from about 0.1% to about 1%, by weight of the chewing gum.

It may be desirable to have a sustained release of the polymeric surface active agent from the chewing gum. This may be accomplished by incorporating a cationic material whose polymeric surface active agent salt is less soluble in water than the sodium, potassium or hydrogen salts. By adding such cationic material, particularly divalent cationic materials such as calcium, the release rate of the polymeric surface active agent may be tailored to a required profile. The maximum level of cationic material incorporated is one cation per monomer unit forming the polymeric surface active agent. The level of cationic material incorporated is more preferably less than 0.5 cations per monomer unit forming the polymeric surface active agent. By weight percent, the polymeric surface active agent is generally present in at least about two times the cationic material, preferably about four times the cationic material, and more preferably at least about five times the cationic material. For example, the cationic material is typically present in an amount of up to about 10%, preferably from about 0.05% to about 5%, and more preferably from about 0.1% to about 3%, by weight of the chewing gum. The particulate polyphosphate material preferred for use in the second aspect of the present invention should have a minimum particle size such that they are retained by a 0.1 mm mesh, preferably a 0.112 mm mesh, more preferably a 0.16 mm mesh, even more preferably a 0.18 mm mesh and most preferably a 0.2 mm mesh wherein the meshes are selected from the DIN 4188 mesh series. Furthermore the solid particulate materials for use in the second aspect of the present invention should have a maximum particle size such that pass through a 2 mm mesh, preferably a 1 mm mesh, more preferably an 0.8 mm mesh, even more preferably a 0.5 mm mesh and most preferably a 0.4 mm mesh, again wherein the meshes are selected from the DIN 4188 mesh series.

The solubility of the particulate polyphosphate preferred for use in the second aspect of the present invention should be at least 5 g per 100 ml at 25° C., preferably of at least 8 g, more preferably at least 10 g, even preferably at least 15 g per 100 ml at 25° C. Thus the solid particulate should be "sparingly soluble", or preferably more soluble, wherein the term is defined as in the British Pharmacopoeia, 1999, Volume 1. Whilst there is no limit on the upper solubility of the polyphosphate it is preferred that it is not freely soluble in water otherwise it will dissolve too rapidly for a crunch to be experienced.

It is preferred that particulate polyphosphate materials for use in the second aspect of the present invention have hardness of greater than 1, preferably of 2 or greater, on the Mohs hardness scale. It is also preferred that the particulate polyphosphate materials for use in the second aspect of this invention are distributed evenly throughout the gum base. Additionally it is also preferred that, according to the second aspect of this invention, that the weight ratio of gum to particulate polyphosphate is in the range from about 10:1 to about 1:10, preferably from about 5:1 to about 1:5, more preferably from about 5:1 to about 1:1.

Additional Chewing Gum Components

In preparing the present chewing gum compositions, it is desirable to add one or more additional chewing gum components. Such materials are well known in the art and are readily chosen by one skilled in the art based on the physical and aesthetic properties desired for the chewing gum compositions being prepared. These carriers may be included at levels which do not interfere or prohibit the surface conditioning. The amount of polymeric surface active agent may be increased to account for the additional components. The additional chewing gum components typically comprise from about 30% to about 99%, preferably from about 40% to about 98%, and more preferably from about 70% to about 95%, by weight of the chewing gum composition.

Additional chewing gum components include carrier materials. The carrier materials are water insoluble materials which are typically not released in the mouth and water soluble materials which are released in the mouth. Water insoluble materials are typically used to form a chewing gum base.

An abrasive polishing material may be included in the chewing gum compositions. The abrasive polishing material contemplated for use in the compositions of the present invention can be any material which does not excessively abrade dentin. The abrasive polishing material should be formulated in the chewing gum composition so that it does not compromise the stability of any ingredients. Typical abrasive polishing materials include silica gels and precipitates; aluminas; water soluble phosphates (including orthophosphates, polymetaphosphates, and pyrophosphates); and mixtures thereof. Specific examples include calcium orthophosphate dihydrate, calcium pyrophosphate, tricalcium phosphate, calcium polymetaphosphate, insoluble sodium polymetaphosphate, hydrated alumina, beta calcium pyrophosphate, calcium carbonate, and resinous abrasive materials such as particulate condensation products of urea and formaldehyde. Mixtures of abrasives may also be used. The abrasive in the chewing gum compositions is generally from about 1% to about 70% and preferably from about 5% to about 50%, by weight of the chewing gum composition.

Another ingredient of the chewing gum composition is an elastomer or elastomer mixture. The elastomers useful in the present composition include styrene-butadiene rubber (SBR) and other elastomeric materials generally known in the art. Illustrative elastomers include SBR, synthetic gums or elastomers such as polyisobutylene and isobutylene-isoprene copolymers; natural gums or elastomers such as chicle, natural rubber, jelutong, balata, guttapercha, lechi caspi, sorva and mixtures thereof. The elastomer or elastomer mixture is generally present in an amount of from 2% to about 30% and preferably from about 5% to about 25% by weight. When the total amount of elastomer is below 2% the base composition lacks elasticity, chewing texture, and cohesiveness whereas at amounts above about 30% the formulation is hard, rubbery and maintains a tight chew.

An optional but desirable ingredient of the chewing gum composition is a resin. The resin serves to plasticise the gum base. Suitable resins for use herein include polyvinyl acetate (PVA) and terpene resins, including polyterpene and polymers of alpha-pinene or beta-pinene, and mixtures thereof. The resin can conveniently be used at a level of from about 3% to about 25%, preferably from about 5% to about 20% by weight of the gum composition.

In addition to the resin component, the gum base compositions of the present invention preferably comprise a plasticiser in an amount up to about 10%, preferably from about 0.1% to about 3% by weight of the gum composition. Suitable plasticisers include glyceryl triacetate, acetylated monoglyceride, glyceryl tributyrate, ethyl laurate, ethyl acetoacetate, diethyl tartrate, ethyl or butyl lactates, diethyl malate, ethyl oleate, castor oil, succinylated monoglycerides or mixtures thereof. Glyceryl triacetate and acetylated monoglyceride are preferred.

Various fats can also be included in the chewing gum compositions of the present invention. Preferred fats include the hydrogenated vegetable oils such as hydrogenated palm oil, hydrogenated soybean oil, hydrogenated cotton seed oil and various other hydrogenated vegetable oils and mixtures thereof. The fats can suitably be used at a level up to about 20%, preferably from about 1% to about 10% by weight of the chewing gum composition.

A further desirable ingredient of the chewing gum base composition is an elastomer solvent. The elastomer solvent aids in softening the elastomer component. Such elastomer solvents include methyl, glycerol or pentaerythritol esters of rosins or modified rosins, such as hydrogenated, dimerized or polymerised rosins or mixtures thereof. Examples of elastomer solvents suitable for use herein include the pentaerythritol ester of partially hydrogenated wood rosin, pentaerythritol ester of wood rosin, glycerol ester of partially dimerized rosin, glycerol ester of polymerised rosin, glycerol ester of tall oil, wood or gum rosin, glycerol ester of partially hydrogenated rosin, methyl ester of partially hydrogenated rosin, and mixtures thereof. The elastomer solvent can be employed in an amount ranging from about 2% to about 50%, preferably from about 10% to about 35% by weight of the chewing gum.

The gum base compositions can also include one or more waxes. Suitable waxes include paraffin wax; microcrystalline wax; Fischer-Tropsch paraffin; natural waxes such as candellilla, carnauba and beeswax; polyolefin waxes such as polyethylene wax; and mixtures thereof. The waxes can be present in levels up to about 25%, preferably from about 5% to about 20% by weight of the gum composition.

The chewing gum also preferably includes an emulsifier. Suitable emulsifiers include glycerol monostearate, lecithin, fatty acid monoglycerides, diglycerides, propylene glycol monostearate and mixtures thereof. The emulsifier is employed in amounts up to about 10% and preferably from about 2% to about 6% by weight of the chewing gum.

A variety of softeners can also be employed in the chewing gum compositions of the present invention. Suitable softeners include fatty materials such as lanolin, stearic acid, sodium stearate and potassium stearate; polyhydric alcohols such as glycerine, propylene glycol, and the like; and mixtures thereof. The softeners can suitably be used at a total level of up to about 30%, preferably from about 0.1% to about 10% by weight of the chewing gum. In a preferred embodiment, the chewing gum composition comprises a fatty softener selected from stearic acid, sodium stearate, potassium stearate and mixtures thereof in an amount of from about 0.1% to about 10% by weight of the chewing gum. Preferably, the fatty softener is stearic acid. The gum base composition may further comprise a polyhydric alcohol. If present, the polyhydric alcohol is present in an amount of from about 0.5% to about 25%, more preferably from about 1% to about 10% by weight of the chewing gum. Such materials, when incorporated into the gum base, assist in modifying the texture and consistency properties. In particular, they help to soften the chew and to maintain chew softness over an extended period of time.

Bulking agents, such as fillers, can also be employed in the chewing gum. Suitable fillers and bulking agents are generally non-abrasive, preferably with an average particle size less than 5 $\mu$m, more preferably less than 3 $\mu$m and especially less than 1 $\mu$m. Illustrative bulking agents include calcium carbonate or ground limestone, talc, aluminium hydroxide, alumina, aluminium silicates, calcium phosphate and mixtures thereof. Where present, the filler can be used in levels up to about 50%, preferably up to about 30%, most preferably from up to about 10% by weight of the chewing gum.

Suitable bulk sweeteners are monosaccharides, disaccharides, and polysaccharides such as xylose, ribose, glucose, mannose, galactose, fructose, dextrose, sucrose, sugar maltose, fructo oligo saccharide syrups, partially hydrolysed starch, or corn syrup solids. Preferred sweetening agents are sugar alcohols such as sorbitol, xylitol, mannitol, maltitol, isomalt, hydrogenated starch hydrolisate, inulin, and other non-carigenic edible polyols such as glycerin and erythritol and mixtures thereof.

In general, the amount of sweetener will vary with the sweetener used and desired amount of sweetener selected for a particular chewing gum. This amount will normally vary from about 0.01% when using a high intensity sweetener to about 80% by weight of the chewing gum composition when using an easily extractable bulk sweetener. The bulk sweeteners described above, are preferably used in amounts of about 10% to about 80% by weight and most preferably about 30% to about 70% by weight. These amounts are ordinarily necessary to achieve a desired level of sweetness independent from the flavor level achieved from the flavoring agents.

In preferred embodiments, the chewing gum composition further comprises a high intensity sweetener. Suitable high intensity sweeteners include: dipeptide based sweeteners such as L-aspartyl-L-phenylalanine methyl ester (Aspartame) and equivalents described in U.S. Pat. No. 3,492,131, L-$\alpha$-aspartyl-N-(2,2,4,4-tetramethyl-3-thietanyl)-D-alaninamide hydrate (Alltame) and the like; the soluble saccharin salts, i.e., sodium or calcium saccharin salts; cyclamate salts, acesulfame-K and the like; the free acid form of saccharin; chlorinated derivatives of sucrose such as chlorodeoxysucrose and the like; and protein based sweeteners, such as Thaumatin (talin). The high intensity sweeteners described can be added in amounts of from about 0.01% to about 2.0% and most preferably from about 0.05% to about 0.5% by weight of the chewing gum composition. Using a high intensity sweetener within the gum base may prolong the flavor of the finished gum composition during chewing.

The chewing gum can also include colorants and pigments, such as titanium dioxide. In general, the gum can contain up to about 2% of pigment and/or colorant. Antioxidants can also be included in the gum, at a level of up to about 0.5%. Suitable anti-oxidants are butylated hydroxyanisole, butylated hydroxytoluene, propyl galate, ascorbic acid and tocopherols.

Flavoring agents well known in the chewing gum art can be added to the chewing gum compositions of the invention. These flavoring agents can be chosen from synthetic flavoring liquid and/or oils derived from plants leaves, flowers, fruits and so forth, and combinations thereof. Representative flavoring liquids include: spearmint oil, cinnamon oil, oil of wintergreen (methylsalicylate) and peppermint oils. Also useful are artificial, natural or synthetic fruit flavors such as citrus oil including lemon, orange, banana, grape, lime, apricot and grapefruit and fruit essences including apple, strawberry, cherry, orange, pineapple and so forth; bean and nut derived flavors such as coffee, cocoa, cola, peanut, almond and so forth. Additionally, flavor adsorbed onto a hdrophillic matrix may be included e.g. "spray-dried" flavors. Furthermore encapsulated flavors may be included. Also included in the term flavorant are sensates and coolants. Preferred coolants include MGA, Physcool, WS-3, WS-23, TK-10, and combinations thereof.

The amount of flavorant employed is normally a matter of preference subject to such factors as flavor type, base type and strength desired. In general, amounts up to about 4% by weight and preferably about 0.05% to about 3.0% by weight of the chewing gum composition are usable with amounts of about 0.8% to about 2.5% being preferred.

Water employed in the preparation of commercially suitable chewing gum compositions should preferably be of low ion content and free of organic impurities. Water will generally comprise less than about 10%, preferably from about 0.01% to about 5%, and more preferably from about 0.1% to about 3%, by weight of the composition herein. The amounts of water include the free water which is added plus that which is introduced with other materials, such as with sorbitol, silica, and solutions.

The present invention may also include other agents, such as antimicrobial agents. The chewing gum composition may include an orally active metallic ion as an antimicrobial agent, particularly salts of zinc, tin and silver and copper.

Other antimicrobial agents include the water insoluble non-cationic antimicrobial agents such as halogenated diphenyl ethers, phenolic compounds including phenol and its homologs, mono and poly-alkyl and aromatic halophenols, resorcinol and its derivatives, bisphenolic compounds and halogenated salicylanilides, benzoic esters, and halogenated carbanilides. The water soluble antimicrobials include quaternary ammonium salts and bis-biquanide salts, among others. Triclosan monophosphate is an additional water soluble antimicrobial agent. The quaternary ammonium agents include those in which one or two of the substitutes on the quaternary nitrogen has a carbon chain length (typically alkyl group) from about 8 to about 20, typically from about 10 to about 18 carbon atoms while the remaining substitutes (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl) ammonium bromide, benzyl dimethylstearyl ammonium chloride, cetyl pyridinium chloride, cetyl pyridinium saccharinate, quaternized 5-amino-1,3-bis(2-ethyl-hexyl)-5-methyl hexa hydropyrimidine, benzalkonium chloride, benzethonium chloride and methyl benzethonium chloride are exemplary of typical quaternary ammonium antibacterial agents. Other compounds are bis[4-(R-amino)-1-pyridinium] alkanes as disclosed in U.S. Pat. No. 4,206,215, issued Jun. 3, 1980, to Bailey, incorporated herein by reference. Other antimicrobials such as copper bisglycinate, copper glysinate, zinc citrate, zinc citrate-maleate, zinc lactate, hexetidine, hexamadine, furanones, and phalimido-peroxycaproic acid may also be included. Also useful are enzymes, including endoglycosidase, papain, dextranase, mutanase, and mixtures thereof. Such agents are disclosed in U.S. Pat. No. 2,946,725, Jul. 26, 1960, to Norris et al. and in U.S. Pat. 4,051,234, Sep. 27, 1977 to Gieske et al., incorporated herein by reference. Specific antimicrobial agents include chlorhexidine, triclosan and its derivatives including triclosan monophosphate, triclosan diphosphate, and phenolated triclosan and flavor oils such as thymol, geraniol, eugenol, and biosol. Triclosan and other agents of this type are disclosed in Parran, Jr. et al., U.S. Pat. No. 5,015,466, issued May 14, 1991, and U.S. Pat. No. 4,894,220, Jan. 16, 1990 to Nabi et al., incorporated herein by reference. These agents may be present at levels of from about 0.01% to about 10%, preferably from about 0.05% to about 5%, and more preferably from about 0.1% to about 2%, by weight of the chewing gum composition.

Optional agents that may be used in combination with the polymeric surface active agent include materials known to be effective in reducing calcium phosphate mineral deposition related to calculus formation. Pyrophosphate salts may be used in the present invention as anticalculus agents or as buffering agents, as long of the surface conditioning effects of the polymeric surface active agent is not eliminated. The amount of pyrophosphate salt useful in making these compositions is any tartar control effective amount, and is generally from about 1.5% to about 15%, preferably from about 2% to about 10%, and most preferably from about 2.5% to about 8%, by weight of the chewing gum composition. Other agents included are synthetic anionic polymers [including polyacrylates and copolymers of maleic anhydride or acid and methyl vinyl ether (e.g., Gantrez), as described, for example, in U.S. Pat. No. 4,627,977, to Gaffar et al., the disclosure of which is incorporated herein by reference in its entirety; as well as, e.g., polyamino propoane sulfonic acid (AMPS)], zinc citrate trihydrate, diphosphonates (e.g., EHDP; AHP), polypeptides (such as polyaspartic and polyglutamic acids), and mixtures thereof.

The present invention may also include buffering agents to adjust the pH of the chewing gum and may help to stabilize the polymeric surface active agent. Other potential ingredients include a fluoride ion source. An alkali metal bicarbonate salt, surfactants, whitening agents such as peroxide or percarbonate, coloring agents, xylitol, thickening materials, binders, humectants, absorbents such as activated carbon, silica absorbents, cyclodextrins, and zeolites and combinations thereof, may also be included in the chewing gum composition.

The chewing gum composition may be in the form of a chiclet or other form that contains a outer coating or shell around the central portion or gum base of the chewing gum. The outer coating may be hard or crunchy. Typically, the outer coating will be comprised of about sorbitol, malitol, xylitol, isomalt, and other crystalisable polyols. The outer coating may also contain small amounts of water and gum arabic. A polyol coating can be further coated with wax. The present invention may have the polymeric surface active agent present in the chewing gum base, the outer coating, or both.

It may be desirable to have a rapid release of the polymeric surface active agent from the chewing gum. This may be accomplished by incorporating some or all of the polymeric surface active agent into the outer coating. To further increase the rate of release of the polymeric surface active agent from the outer coating, the particles are processed in a manner to result in a microporous sized porosity.

Method of Treatment

The present invention relates to methods for providing surface conditioning effects. The present invention also relates to methods of providing clean mouth and tooth feel, smooth teeth feel, and longer lasting clean or smooth tooth feel. Additional efficacy, such as reduced gingivitis, plaque, calculus, and sensitivity, and improved breath may also occur depending upon the composition of the chewing gum. The benefits of these compositions may increase over time when the composition is repeatedly used.

The method of treatment herein comprises contacting a subject's dental enamel surfaces and mucosa in the mouth with the chewing gum compositions according to the present invention. The method of treatment will typically be by chewing the gum. The subject may be any person or lower animal whose tooth surface contact the chewing gum composition.

Examples & Method of Manufacturing

The following examples further describe and demonstrate embodiments within the scope of the present invention. These examples are given solely for the purpose of illustration and are not to be construed as limitations of the present invention as many variations thereof are possible without departing from the spirit and scope.

Making Instructions

Products A, B

Heat gum base to ~45° C. to soften. Maintain mixer vessel cavity at ~45° C. during entire mixing process. Add gum base to mixing cavity of double sigma blade mixer and mix for 5 minutes. Add mannitol and spray-dried menthol. Mix for 2 minutes. Add glycerin and mix for 2 minutes. Add 50% of xylitol and mix for 2 minutes. Add hydrogenated starch hydrolisate and mix for 5 minutes. Add 50% sorbitol and mix for 3 minutes. Add second 50% of xylitol, Glass-H and aspartame and mix for 3 minutes. Add flavor and mix for 3 minutes.

| Material Name (INCI) | A | B | C Core | C Coating | D Core | D Coating |
|---|---|---|---|---|---|---|
| Sorbitol | 25.850 | 18.350 | 33.350 | | 33.350 | |
| Xylitol | 16.700 | 16.700 | 16.700 | | 16.700 | |
| Gum base (e.g. Prestige-PL, Cafosa) | 28.000 | 28.000 | 28.000 | | 28.000 | |
| Sodium polyphosphate, n = 21; Glass H (FMC) | 7.500 | 15.000 | 0.000 | 37.500 | 0.000 | |
| Glass H (microporous sized) | | | | | | 37.500 |
| Hydrogenated starch hydrolisate (85% solids) | 8.000 | 8.000 | 8.000 | | 8.000 | |
| Glycerin | 7.000 | 7.000 | 7.000 | | 7.000 | |
| Mannitol | 5.000 | 5.000 | 5.000 | | 5.000 | |
| Maltitol | | | | 62.250 | | 62.250 |
| Ethyl cellulose (Ethocell, Dow Corning) | | | | | | |
| Zinc lactate dihydrate | | | | | | |
| Sodium polyphosphate, n = 6; Sodaphos (FMC) | | | | | | |
| Sodium polyphosphate, n = 13; Hexaphos (FMC) | | | | | | |
| Poloxamer 407 | | | | | | |
| Flavor | 1.600 | 1.600 | 1.600 | 0.250 | 1.600 | 0.250 |
| Aspartame | 0.200 | 0.200 | 0.200 | | 0.200 | |
| Spray dried flavor | 0.150 | 0.150 | 0.150 | | 0.150 | |
| TOTAL | 100.000 | 100.000 | 100.000 | 100.000 | 100.000 | 100.000 |
| % OF TOTAL COMPOSITION | 100.000 | 100.000 | 80.000 | 20.000 | 80.000 | 20.000 |

| Material Name (INCI) | E | F | G | H | I | J | K |
|---|---|---|---|---|---|---|---|
| Sorbitol | 15.850 | 25.123 | 18.350 | 23.350 | 23.850 | 23.850 | 24.719 |
| Xylitol | 16.700 | 16.700 | 16.700 | 16.700 | 16.700 | 16.700 | 16.700 |
| Gum base (e.g. Prestige-PL, Cafosa) | 28.000 | 28.000 | 28.000 | 28.000 | 28.000 | 28.000 | 28.000 |
| Sodium polyphosphate, n = 21; Glass H (FMC) | 7.500 | 7.500 | | | 7.500 | 7.500 | 7.500 |
| Hydrogenated starch hydrolisate (85% solids) | 8.000 | 8.000 | 8.000 | 8.000 | 8.000 | | 8.000 |
| Glycerin | 7.000 | 7.000 | 7.000 | 7.000 | 7.000 | 7.000 | 7.000 |
| Mannitol | 5.000 | 5.000 | 5.000 | 5.000 | 5.000 | 5.000 | 5.000 |
| Maltitol | | | | | | 8.000 | |
| Ethyl cellulose (Ethocell, Dow Corning) | 10.000 | | | | | | |
| Zinc lactate dihydrate | | 0.727 | | | | | |
| Sodium polyphosphate, n = 6; Sodaphos (FMC) | | | 15.000 | | | | |
| Sodium polyphosphate, n = 13; Hexaphos (FMC) | | | | 10.000 | | | |
| Poloxamer 407 | | | | | 2.000 | 2.000 | |
| Flavor | 1.600 | 1.600 | 1.600 | 1.600 | 1.600 | 1.600 | 1.600 |
| Aspartame | 0.200 | 0.200 | 0.200 | 0.200 | 0.200 | 0.200 | 0.200 |
| Spray dried flavor | 0.150 | 0.150 | 0.150 | 0.150 | 0.150 | 0.150 | 0.150 |
| Calcium chloride | | | | | | | 0.754 |
| TOTAL | 100.000 | 100.00 | 100.00 | 100.000 | 100.000 | 100.000 | 100.000 |
| % OF TOTAL COMPOSITION | 100.000 | 100.00 | 100.00 | 100.000 | 100.000 | 100.000 | 100.000 |

Products C, D

Heat gum base to ~45° C. to soften. Maintain mixer vessel cavity at ~45° C. during entire mixing process. Add gum base to mixing cavity of double sigma blade mixer and mix for 5 minutes. Add mannitol and spray-dried menthol. Mix for 2 minutes. Add glycerin and mix for 2 minutes. Add 50% of xylitol and mix for 2 minutes. Add hydrogenated starch hydrolisate and mix for 5 minutes. Add 50% sorbitol and mix for 3 minutes. Add second 50% of xylitol aspartame and mix for 3 minutes. Add flavor and mix for 3 minutes. Store for ~1 week at 15–20° C., 30–60% RH (conditioning). Tumble chewing gums in coater-drier with maltitol solution and Glass-H. Maintain tumbling until surface is dry.

Product E

Heat gum base to ~45° C. to soften. Maintain mixer vessel cavity at ~45° C. during entire mixing process. Add gum base to mixing cavity of double sigma blade mixer and mix for 5 minutes. Add mannitol and spray-dried menthol. Mix for 2 minutes. Add glycerin and mix for 2 minutes. Add 50% of xylitol and mix for 2 minutes. Add hydrogenated starch hydrolisate and mix for 5 minutes. Add 50% sorbitol and mix for 3 minutes. Add second 50% of xylitol, Glass-H in encapsulated ethyl celullose and aspartame and mix for 3 minutes. Add flavor and mix for 3 minutes.

Product F

Heat gum base to –45° C. to soften. Maintain mixer vessel cavity at ~45° C. during entire mixing process. Add gum base to mixing cavity of double sigma blade mixer and mix for 5 minutes. Add mannitol and spray-dried menthol. Mix for 2 minutes. Add glycerin and mix for 2 minutes. Add 50% of xylitol and mix for 2 minutes. Add hydrogenated starch hydrolisate and mix for 5 minutes. Add 50% sorbitol and mix for 3 minutes. Add second 50% of xylitol, Glass-H, zinc lactate, and aspartame and mix for 3 minutes. Add flavor and mix for 3 minutes.

Product G, H

Heat gum base to ~45° C. to soften. Maintain mixer vessel cavity at ~45° C. during entire mixing process. Add gum base to mixing cavity of double sigma blade mixer and mix for 5 minutes. Add mannitol and spray-dried menthol. Mix for 2 minutes. Add glycerin and mix for 2 minutes. Add 50% of xylitol and mix for 2 minutes. Add hydrogenated starch hydrolisate and mix for 5 minutes. Add 50% sorbitol and mix for 3 minutes. Add second 50% of xylitol, sodaphos, hexaphos, and aspartame and mix for 3 minutes. Add flavor and mix for 3 minutes.

Product I

Heat gum base to ~45° C. to soften. Maintain mixer vessel cavity at ~45° C. during entire mixing process. Add gum base to mixing cavity of double sigma blade mixer and mix for 5 minutes. Add mannitol and spray-dried menthol. Mix for 2 minutes. Add glycerin and mix for 2 minutes. Add 50% of xylitol and mix for 2 minutes. Add hydrogenated starch hydrolisate and mix for 5 minutes. Add 50% sorbitol and mix for 3 minutes. Add second 50% of xylitol, Glass-H, Poloxamer 407, and aspartame and mix for 3 minutes. Add flavor and mix for 3 minutes.

Product J

Heat gum base to ~45° C. to soften. Maintain mixer vessel cavity at ~45° C. during entire mixing process. Add gum base to mixing cavity of double sigma blade mixer and mix for 5 minutes. Add mannitol and spray-dried menthol. Mix for 2 minutes. Add glycerin and mix for 2 minutes. Add 50% of xylitol and mix for 7 minutes. Add 50% sorbitol and mix for 3 minutes. Add second 50% of xylitol, Glass-H and aspartame and mix for 3 minutes. Add flavor and mix for 3 minutes.

Product K

Heat gum base to ~45° C. to soften. Maintain mixer vessel cavity at ~45° C. during entire mixing process. Add gum base to mixing cavity of double sigma blade mixer and mix for 5 minutes. Add mannitol and spray-dried menthol. Mix for 2 minutes. Add glycerin and mix for 2 minutes. Add 50% of xylitol and mix for 2 minutes. Add hydrogenated starch hydrolisate and mix for 5 minutes. Add 50% sorbitol, calcium chloride and mix for 3 minutes. Add second 50% of xylitol, Glass-H and aspartame and mix for 3 minutes. Add flavor and mix for 3 minutes.

What is claimed is:

1. A chewing gum composition including water soluble and water insoluble components and comprising:
   a. from about 0.1% to about 50% of a particulate polymeric surface active agent having:
      (i) a particle size such that a particle of said polymeric surface active agent passes through a 2 mm mesh and is retained by a 0.1 mm mesh;
      (ii) an aqueous solubility of at least 5 g per 100 ml at 25° C.;
   b. up to about 10% of water; and
   c. from about 40% to about 99% of carrier materials,
   wherein said particulate polymeric surface active agent provides a crunchy texture which lasts throughout the initial minutes of mastication and disappears over time leaving no gritty residue, and surface conditioning effects of a subject's teeth and mucosal surfaces including (a) increased hydrophilic surface on teeth and a hydrophobic surface on the mucosa as measured by changed water contact angles, (b) increased total surface energy of teeth, (c) increased Lewis base score and (d) description of adsorbed pellicle proteins, thereby conferring improved intraoral cleaning and smooth tooth feel impression.

2. The chewing gum composition according to claim 1 wherein the chewing gum has an outer coating.

3. The chewing gum composition according to claim 1 where the chewing gum further comprises a cationic material.

4. The chewing gum composition according to claim 3 wherein the cationic material controls the release rate of the polymeric surface active agent.

5. The chewing gum composition according to claim 3 wherein the cationic material is calcium.

6. The chewing gum composition according to claim 1 wherein the polymeric surface active agent is a glass polyphosphate.

7. The chewing gum composition according to claim 6 wherein the glassy polyphosphate has an average chain length of about 21.

8. The chewing gum composition according to claim 1 wherein the chewing gum further comprises an orally active astringency-conferring metallic ion.

9. The chewing gum composition according to claim 8 wherein the astringency of the chewing gum is reduced by the polymeric surface active agent.

10. The chewing gum composition according to claim 9 wherein the efficacy of the orally active metallic ion is not significantly reduced by the polymeric surface active agent.

11. A method of providing a crunchy texture and surface conditioning effects to a subject's teeth and oral mucosa comprising administering to the subject a chewing gum composition according to claim 1.

12. A method of reducing astringency of a chewing gum composition containing an orally active metallic ion comprising administering to the subject the chewing gum composition including water-soluble and water insoluble components and comprising:

a. from about 0.1% to about 50% of a particulate polymeric surface active agent having:
   (i) a particle size such that a particle of said polymeric surface active agent passes through a 2 mm mesh and is retained by a 0.1 mm mesh;
   (ii) an aqueous solubility of at least 5 g per 100 ml at 25° C.;
b. from about 0.01% to about 10% of an orally active astringency conferring metallic ion;
c. up to about 10% of water; and
d. from about 30% to about 99% of carrier materials;
wherein the efficacy of the orally active metallic ion is not significantly reduced by the polymeric surface active agent.

13. A chewing gum comprising:
   a. from about 0.1% to about 50% of a particulate polyphosphate that provides surface conditioning effects and a crunchy texture which lasts throughout the initial minutes of mastication and disappears over time leaving no gritty residue, wherein the particulate polyphosphate;
      (i) has a particle size such that a particle of said polyphosphate passes through a 2 mm mesh and is retained by a 0.1 mm mesh;
      (ii) has an aqueous solubility of at least 5 g per 100 ml at 25° C.; and
   b. greater than about 10% gum base comprising one or more elastomers, resins or waxes and mixtures thereof.

14. A composition according to claim 13 which comprises from about 0.5% to about 30%, by weight, of particulate polyphosphate.

15. A composition according to claim 13 which comprises from about 1% to about 15%, by weight, of particulate polyphosphate.

16. A composition according to claim 13 which comprises from about 5% to about 12%, by weight, of particulate polyphosphate.

17. A composition according to claim 13 wherein the particulate polyphosphate has a particle size such that it passes through a 1 mm mesh.

18. A composition according to claim 13 wherein the particulate polyphosphate has a particle size such that is passes through a 0.8 mm mesh.

19. A composition according to claim 13 wherein the particulate polyphosphate has a particle size such that is passes through 0.5 mm mesh.

20. A composition according to claim 13 wherein the particulate polyphosphate has a particle size such that is passes through a 0.4 mm mesh.

21. A composition according to claim 13 wherein the particulate polyphosphate has a particle size such that it is retained by a 0.112 mm mesh.

22. A composition according to claim 13 wherein the particulate polyphosphate has a particle size such that it is retained by a 0.16 mm mesh.

23. A composition according to claim 13 wherein the particulate polyphosphate has a particle size such that it is retained by a 0.18 mm mesh.

24. A composition according to claim 13 wherein the particulate polyphosphate has a particle size such that it is retained by a 0.2 mm mesh.

25. A composition according to claim 13 wherein the particulate polyphosphate is sodium polyphophate with an average chain length of from about 10 to about 30.

26. A composition according to claim 13 wherein the particulate polyphosphate is sodium polyphosphate with an average chain length of from about 15 to 25.

27. A composition according to claim 13 wherein the particulate polyphosphate is sodium polyphosphate with an average chain length of from about 21 to about 23.

28. A composition according to claim 13 wherein the particulate polyphosphate has an aqueous solubility of at least about 8 g per 100 ml at 25° C.

29. A composition according to claim 13 wherein the particulate polyphosphate has an aqueous solubility of at least about 10 g per 100 ml at 25° C.

30. A composition according to claim 13 wherein the particulate polyphosphate has an aqueous solubility of at least about 15 g per 100 ml at 25° C.

31. A composition according to claim 13 wherein the particulate polyphosphate has a hardness of greater than 1 when measured using the Mohs hardness scale.

32. A composition according to claim 13 wherein the particulate polyphosphate has a hardness of 2 or greater when measured using the Mohs hardness scale.

33. A composition according to claim 13 wherein the particulate polyphosphate is dispersed throughout the chewing gum composition.

34. A composition according to claim 13 wherein the weight ratio of gum to particulate polyphosphate is in the range from about 10:1 to about 1:10.

35. A composition according to claim 13 wherein the weight ratio of gum to particulate polyphosphate is in the range from about 5:1 to about 1:5.

36. A composition according to claim 13 wherein the weight ratio of gum to particulate polyphosphate is in the range from about 5:1 to about 1:1.

37. A method of providing a crunchy texture and surface conditioning effects to a subject's teeth and oral mucosa comprising administering to the subject a chewing gum composition according to claim 13.

* * * * *